United States Patent
Patcas et al.

(10) Patent No.: US 10,336,667 B2
(45) Date of Patent: Jul. 2, 2019

(54) CATALYST FOR DEHYDROGENATING HYDROCARBONS

(71) Applicant: BASF SE, Ludwigshafen (DE)

(72) Inventors: Florina C. Patcas, Ludwigshafen (DE); Martin Dieterle, Ludwigshafen (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/309,014

(22) PCT Filed: May 6, 2015

(86) PCT No.: PCT/EP2015/059908
§ 371 (c)(1),
(2) Date: Nov. 4, 2016

(87) PCT Pub. No.: WO2015/169826
PCT Pub. Date: Nov. 12, 2015

(65) Prior Publication Data
US 2017/0073284 A1    Mar. 16, 2017

(30) Foreign Application Priority Data
May 9, 2014  (EP) .................................. 14167662

(51) Int. Cl.
*B01J 23/78*  (2006.01)
*C07C 5/333*  (2006.01)
(Continued)

(52) U.S. Cl.
CPC ........... *C07C 5/3332* (2013.01); *B01J 23/002* (2013.01); *B01J 23/83* (2013.01); *B01J 23/888* (2013.01);
(Continued)

(58) Field of Classification Search
CPC ...... B01J 23/002; B01J 23/83; B01J 23/8872; B01J 23/888; B01J 37/0018; B01J 37/04;
(Continued)

(56) References Cited

U.S. PATENT DOCUMENTS 4,460,706 A   7/1984  Imanari et al.
4,758,543 A   7/1988  Sherrod et al.
(Continued)

FOREIGN PATENT DOCUMENTS

CA   2298227 A1   8/2000
CN   1765495 A    5/2006
(Continued)

OTHER PUBLICATIONS

Li, Phase behavior of iron oxide doping with ethylbenzene dehydrogenation catalyst promoters, 2009, Iowa State University Digital Repository.*

(Continued)

*Primary Examiner* — Patricia L. Hailey
(74) *Attorney, Agent, or Firm* — Drinker Biddle & Reath LLP

(57) ABSTRACT

The present invention relates to a catalyst for the dehydrogenation of hydrocarbons which is based on iron oxide and a process for producing it. The catalyst comprises at least one iron compound, at least one potassium compound and from 11 to 24% by weight of at least one cerium compound, calculated as $CeO_2$, wherein the at least one iron compound and the at least one potassium compound are at least partly present in the form of one or more K/Fe mixed oxide phases of the general formula $K_xFe_yO_z$, where x is from 1 to 17; y is from 1 to 22 and z is from 2 to 34, and comprises at least 50% by weight, based on the total catalyst, of the K/Fe mixed oxide phases, and also a process for producing it.

11 Claims, 1 Drawing Sheet

(51) Int. Cl.
*B01J 37/04* (2006.01)
*B01J 23/00* (2006.01)
*B01J 23/83* (2006.01)
*B01J 23/887* (2006.01)
*B01J 23/888* (2006.01)
*B01J 37/00* (2006.01)

(52) U.S. Cl.
CPC ....... *B01J 23/8872* (2013.01); *B01J 37/0018* (2013.01); *B01J 37/04* (2013.01); *B01J 2523/00* (2013.01); *C07C 2521/06* (2013.01); *C07C 2523/02* (2013.01); *C07C 2523/04* (2013.01); *C07C 2523/10* (2013.01); *C07C 2523/22* (2013.01); *C07C 2523/28* (2013.01); *C07C 2523/30* (2013.01); *C07C 2523/745* (2013.01); *C07C 2523/78* (2013.01); *C07C 2523/83* (2013.01); *C07C 2523/887* (2013.01); *C07C 2523/888* (2013.01)

(58) Field of Classification Search
CPC ............... B01J 2523/00; C07C 5/3332; C07C 2521/06; C07C 2523/02; C07C 2523/04; C07C 2523/10; C07C 2523/22; C07C 2523/28; C07C 2523/30; C07C 2523/745; C07C 2523/78; C07C 2523/83; C07C 2523/887; C07C 2523/888
USPC .......... 502/328, 330, 338; 585/440, 444, 654
See application file for complete search history.

(56) References Cited

U.S. PATENT DOCUMENTS

| | | | | |
|---|---|---|---|---|
| 5,824,831 | A * | 10/1998 | Shiraki | B01J 23/78 585/444 |
| 6,028,027 | A | 2/2000 | Baier et al. | |
| 6,177,602 | B1 * | 1/2001 | Williams | B01J 23/894 585/444 |
| 6,184,174 | B1 * | 2/2001 | Rubini | B01J 23/8871 502/304 |
| 6,222,085 | B1 * | 4/2001 | Shiraki | B01J 23/78 502/330 |
| 6,551,958 | B1 | 4/2003 | Baier et al. | |
| 6,756,339 | B1 * | 6/2004 | Rokicki | B01J 23/894 502/304 |
| 6,841,712 | B1 * | 1/2005 | Iezzi | B01J 8/0055 585/440 |
| 8,003,837 | B2 * | 8/2011 | Walsdorff | B01J 23/745 502/336 |
| 2004/0235652 | A1 * | 11/2004 | Smith | B01J 23/002 502/304 |
| 2009/0281256 | A1 * | 11/2009 | Kowaleski | B01J 23/825 526/75 |
| 2010/0087694 | A1 | 4/2010 | Mishima | |
| 2013/0165723 | A1 | 6/2013 | Patcas et al. | |
| 2017/0121241 | A1 * | 5/2017 | Patcas | C07C 5/3332 |

FOREIGN PATENT DOCUMENTS

| | | | |
|---|---|---|---|
| EP | 0181999 | A1 | 5/1986 |
| EP | 0894528 | A2 | 2/1999 |
| EP | 1027928 | A1 | 8/2000 |
| EP | 2106852 | A1 * | 7/2009 ............. B01J 23/88 |
| EP | 2106852 | A1 | 10/2009 |
| JP | S58177148 | A | 10/1983 |
| JP | 2000296335 | A | 10/2000 |
| JP | 2008183492 | A | 8/2008 |
| RU | 2302293 | C1 | 7/2007 |
| RU | 2325229 | C1 | 5/2008 |
| RU | 2385313 | C2 | 3/2010 |
| WO | WO-9710898 | A1 | 3/1997 |
| WO | WO-9949966 | A1 | 10/1999 |
| WO | WO-2013093824 | A1 | 6/2013 |
| WO | WO-2013159251 | A1 | 10/2013 |

OTHER PUBLICATIONS

Dulamiță, N., et al., "Ethylbenzene dehydrogenation on Fe2O3—Cr2O3—K2CO3 catalysts promoted with transitional metal oxides", Applied Catalysis A: General, vol. 287, No. 1, (2005), pp. 9-18.

Hirano, T., "Dehydrogenation of ethylbenzene over potassium-promoted iron oxide containing cerium and molybdenum oxides", Applied Catalysis, vol. 28, (1986), pp. 119-132.

International Search Report for PCT/EP2015/059907 dated Aug. 31, 2015.

International Search Report for PCT/EP2015/059908 dated Jul. 22, 2015.

Liao, S-J., et al., "Effecst of $TiO_2$ on the structure and catalytic behavior of iron-potassium oxide catalyst for dehydrogenation of ethylbenzene to styrene", Catalysis Communications, vol. 9, No. 9, (2008), pp. 1817-1821.

Written Opinion and International Preliminary Report on Patentability for PCT/EP2015/059908 dated Nov. 15, 2016.

Russian Office Action dated Dec. 12, 2018, during the prosecution of Russian application No. 2016148232, which corresponds to the above referenced application.

English Translation of Japanese Office Action for Japanese Application No. 2016-567186, dated Feb. 12, 2019.

* cited by examiner

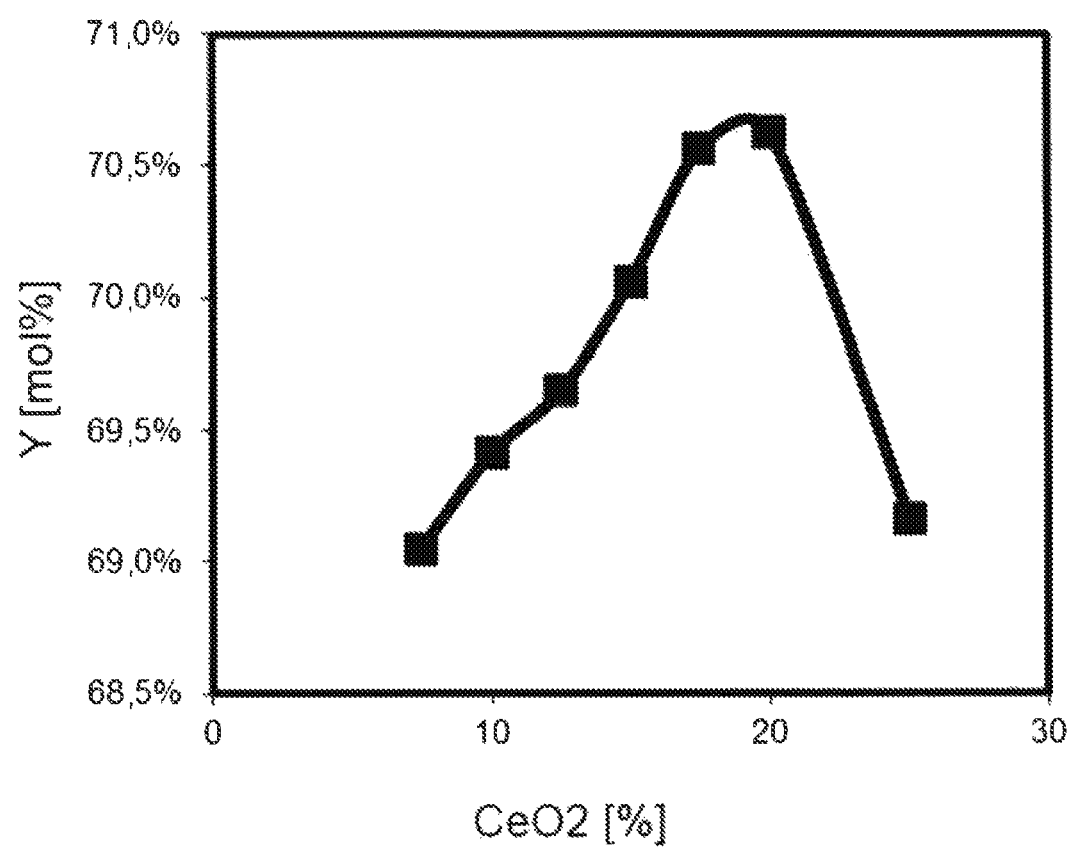

CATALYST FOR DEHYDROGENATING HYDROCARBONS

CROSS-REFERENCE TO RELATED APPLICATIONS

This application is a national stage application (under 35 U.S.C. § 371) of PCT/EP2015/059908, filed May 6, 2015, which claims benefit of European Application No. 14167662.7, filed May 9, 2014, both of which are incorporated herein by reference in their entirety.

The present invention relates to a catalyst for the dehydrogenation of hydrocarbons which is based on iron oxide and a process for producing it. The catalyst comprises at least one iron compound, at least one potassium compound and from 11 to 24% by weight of at least one cerium compound, calculated as $CeO_2$, wherein the at least one iron compound and the at least one potassium compound are at least partly present in the form of one or more K/Fe mixed oxide phases of the general formula $K_xFe_yO_z$, where x is from 1 to 17; y is from 1 to 22 and z is from 2 to 34, and comprises at least 50% by weight, based on the total catalyst, of the K/Fe mixed oxide phases.

The present invention further relates to a process for the catalytic dehydrogenation of hydrocarbons using the catalyst of the invention.

The use of iron oxide-based catalysts in the dehydrogenation of various hydrocarbons to form the corresponding unsaturated hydrocarbons has been known for a long time in the prior art. The dehydrogenation of ethylbenzene to styrene, of isopropylbenzene to alpha-methylstyrene, of butene to butadiene or of isoamylene to isoprene, for example, are of industrial importance. The preparation of styrene by heterogeneously catalyzed dehydrogenation of ethylbenzene in the presence of steam is a process which has been carried out industrially since the beginning of the 1930s and has become established as synthetic route to styrene. Styrene is one of the most important monomers of the plastics industry and is, for example, used for the preparation of polystyrene, acrylonitrile-butadiene-styrene polymer (ABS) and synthetic rubber.

The iron oxide-based dehydrogenation catalysts described in the prior art are generally multicomponent systems and comprise essentially iron oxide and an alkali metal compound which is, for example, used as alkali metal oxide, carbonate or hydroxide in the production of the catalyst. In addition, these catalysts generally comprise various further active components (promoters), for example oxides of the elements of transition groups 5 and 6 of the Periodic Table or of the rare earths. For example, the use of cerium compounds as promoter for such iron oxide-based dehydrogenation catalysts has been described in the prior art.

The catalytic dehydrogenation of aliphatic or alkylaromatic hydrocarbons is usually carried out industrially in the presence of steam at temperatures in the range from 500 to 700° C. In these processes, the hydrocarbon and the steam are typically mixed and passed over the iron oxide dehydrogenation catalyst at elevated temperatures.

As a result of the formation of carbonaceous material, the active sites of the dehydrogenation catalyst typically become blocked during the course of the dehydrogenation process and gradual deactivation of the catalyst occurs. To decrease this deactivation, steam is generally added to the hydrocarbon. The steam enables the carbonaceous material formed on the catalyst surface to be gasified in-situ, as a result of which the active catalyst surface can be regenerated. In addition, the steam typically also has the following functions: provision of the heat of reaction necessary for the endothermic dehydrogenation reaction, shifting of the equilibrium to the product side by reduction of the partial pressures of the starting materials, maintenance of the oxidation state of the iron in the presence of the reducing action of hydrogen and hydrocarbon.

Numerous dehydrogenation catalysts based on iron oxide have been described in the prior art.

EP-A 0 181 999 describes dehydrogenation catalysts comprising iron oxide, potassium oxide, magnesium oxide and optionally further metal compounds. The optional addition of from 0 to 10% by weight of a compound of cerium, molybdenum, tungsten or mixtures thereof, inter alia, is described. The examples of EP-A 0 181 999 describe dehydrogenation catalysts comprising about 6% by weight of cerium dioxide. The catalysts described in EP-A 0 181 999 are said to have, in particular, an improved stability toward boiling water.

The scientific publication by Hirano et al. (Appl. Catal. 28, 1986, p. 119-130) examines the use of cerium as promoter in an iron oxide-potassium oxide catalyst. The publication states that the addition of 5% by weight of cerium dioxide to an iron oxide-potassium oxide catalyst decreases the activation energy in the conversion of ethylbenzene into styrene and increases the reaction rate.

The document U.S. Pat. No. 4,460,706 describes dehydrogenation catalysts comprising from 40 to 87.5% by weight of $Fe_2O_3$, from 11 to 50% by weight of cerium oxide, calculated as $Ce_2O_3$ and from 1.5 to 40% by weight of $K_2O$. The experimental examples of U.S. Pat. No. 4,460,706 describe results of catalytic dehydrogenation using catalysts having different proportions of $Ce_2O_3$, which indicates an optimal, in respect of the styrene yield, cerium oxide content, calculated as $Ce_2O_3$, of 13.2% by weight, corresponding to about 13.8% by weight of $CeO_2$. The presence of potassium-iron mixed oxide phases in the dehydrogenation catalysts is not described.

The document U.S. Pat. No. 4,758,543 describes dehydrogenation catalysts comprising from 5 to 30% by weight of iron, as $Fe_2O_3$, from 40 to 60% by weight of potassium, as $K_2CO_3$, and from 10 to 60% by weight of cerium, as $Ce_2O_3$. The examples of U.S. Pat. No. 4,758,543 describe preferred catalysts comprising from about 10 to 20% by weight of cerium, as $Ce_2O_3$. The presence of potassium-iron mixed oxide phases in the dehydrogenation catalysts is not described.

The document EP 0 894 528 describes catalysts for the dehydrogenation of ethylbenzene which comprise iron oxides, potassium oxide, magnesium oxide and/or calcium oxide, cerium oxide and also tungsten and/or molybdenum oxide, with the catalyst being said to comprise potassium ferrates having a crystallite size of less than 2 μm. The cerium oxide, calculated as $CeO_2$, can be comprised in an amount in the range from 2 to 10% by weight. The examples of EP 0 894 528 describe catalysts comprising 7% by weight of $CeO_2$. The catalysts according to EP 0 894 528 are produced in a 2-stage process in order to make formation of the potassium ferrates described possible.

The document U.S. Pat. No. 6,551,958 discloses catalysts comprising from 50 to 90% by weight of $Fe_2O_3$, from 1 to 40% by weight of $K_2O$, from 5 to 20% by weight of $Ce_2O_3$, from 0.1 to 10% by weight of MgO and from 1 to 10% by weight of CaO. The catalyst according to U.S. Pat. No. 6,551,958 can comprise one or more mixed oxides of the formula $K_2O\cdot(Fe_2O_3)_n$, where n is a natural number in the range from 1 to 11.

There is a need for further-improved dehydrogenation catalysts for the dehydrogenation of hydrocarbons, in particular for the dehydrogenation of ethylbenzene, which have an improved catalyst activity combined with improved or equal stability and operating life. It is an object of the present invention to provide an improved dehydrogenation catalyst based on iron oxide, which, in particular, has an improved catalyst activity, in particular gives an increased yield. The catalyst should likewise have a satisfactory mechanical stability and resistance to boiling water.

A further object of the present invention is to provide processes for producing the improved dehydrogenation catalysts, which processes are simple, inexpensive and reliable to carry out; in particular as few as possible and no complicated process steps such as a sol-gel process should be required.

It has now surprisingly been found that a further improvement in the catalytic properties can be achieved by optimization of the cerium content in combination with a high proportion of K/Fe mixed oxide phases. It has been found that optimized dehydrogenation yields, in particular styrene yields, can be obtained when the catalysts have a high content of K/Fe mixed oxide phases of at least 50% by weight and at the same time comprise from 11 to 24% by weight of at least one cerium compound, calculated as $CeO_2$. It has been able to be shown that a combination of the two features is necessary in order to ensure high catalyst activities combined with good mechanical and chemical stability. It has been able to be shown that, in contrast to the prior art hitherto, the content of cerium dioxide as activity promoter should not be increased beyond a particular value after which the content of the K/Fe mixed oxide phases drops below the preferred value of 50% by weight.

The invention provides a dehydrogenation catalyst comprising at least one iron compound, at least one potassium compound and from 11 to 24% by weight, preferably from 12.5 to 22% by weight, particularly preferably from 15 to 20% by weight, based on the total catalyst, of at least one cerium compound, calculated as $CeO_2$, wherein the at least one iron compound and the at least one potassium compound are at least partly present in the form of one or more K/Fe mixed oxide phases of the general formula $K_xFe_yO_z$, where x is from 1 to 17; y is from 1 to 22 and z is from 2 to 34, where the catalyst comprises at least 50% by weight, preferably at least 60% by weight, particularly preferably at least 65% by weight, based on the total catalyst, of the K/Fe mixed oxide phases.

The invention provides a dehydrogenation catalyst comprising at least one iron compound, at least one potassium compound and from 11 to 24% by weight, preferably from 12.5 to 22% by weight, particularly preferably from 15 to 20% by weight, based on the total catalyst, of at least one cerium compound, calculated as $CeO_2$, wherein the at least one iron compound and the at least one potassium compound are at least partly present in the form of one or more K/Fe mixed oxide phases of the general formula $K_xFe_yO_z$, where x is from 1 to 17; y is from 1 to 22 and z is from 2 to 34, where the catalyst comprises at least 50% by weight, preferably at least 60% by weight, particularly preferably at least 65% by weight, based on the total catalyst, of the one or more K/Fe mixed oxide phases.

BRIEF DESCRIPTION OF THE FIGURE

FIG. 1 shows the styrene yield Y [%] as a function of the proportion of $CeO_2$ in % by weight [% $CeO_2$] in the catalyst.

It can very clearly be seen that an optimal styrene yield can be obtained in the range from 11 to 24% by weight of $CeO_2$.

Unless indicated otherwise, all the following figures in % by weight are based on the total dehydrogenation catalyst and are in each case calculated on the basis of the metal oxide in the highest oxidation state. For the purposes of the present invention, ppm means milligram per kilogram (mg/kg).

The catalysts of the invention display an improved activity compared to the catalysts described in the prior art.

For the purposes of the present invention, dehydrogenation catalyst comprising at least one iron compound, at least one potassium compound, at least one cerium compound and optionally further metal compounds means that the respective metals can be determined in the optionally indicated amounts in the catalyst. Mixed phases (e.g. oxide mixed phases) and/or isolated phases of the metal compounds described below can typically be present in the catalyst. It is additionally possible for one or more of the component(s) described below to be partly or entirely comprised in a different raw material used in catalyst production.

According to the invention, the dehydrogenation catalyst comprises at least one iron compound or at least one iron compound is used in the production of the dehydrogenation catalyst. The at least one iron compound is preferably selected from among natural or synthetic iron oxides and/or iron oxide hydroxides. In particular, the at least one iron compound is selected from the group consisting of $\alpha$-$Fe_2O_3$ (hematite), $\gamma$-$Fe_2O_3$, iron oxide hydroxide (e.g. $\alpha$-FeOOH, goethite) and $Fe_3O_4$ (magnetite). As synthetic iron oxides, it is possible to use, for example, iron oxides which have been produced by thermal decomposition of iron salt solutions.

Preference is given to using an iron oxide, in particular $Fe_2O_3$, preferably $\alpha$-$Fe_2O_3$ (hematite), as iron compound. Preference is also given to the use of $\alpha$-$Fe_2O_3$ (hematite) in combination with goethite (FeOOH) and/or magnetite ($Fe_3O_4$) as iron compound. The proportion of goethite (FeOOH) and/or magnetite ($Fe_3O_4$) is then typically from 0 to 30% by weight, based on the total amount of the iron compounds.

The specific surface area of the iron compound (e.g. determined by means of the BET method) is typically in the range from 1 to 50 m$^2$/g, preferably from 1 to 20 m$^2$/g.

The at least one iron compound is typically comprised in an amount in the range from 50 to 80% by weight, preferably from 60 to 80% by weight, particularly preferably from 65 to 75% by weight, calculated as $Fe_2O_3$, in the dehydrogenation catalyst (based on the total weight of the dehydrogenation catalyst).

According to the invention, the catalyst comprises at least one potassium compound or at least one potassium compound is used in the production of the dehydrogenation catalyst. The at least one potassium compound is preferably selected from among potassium oxide, potassium carbonate, potassium hydroxide, potassium hydrogencarbonate, potassium oxalate and K/Fe mixed oxide phases, in particular selected from among potassium oxide, potassium carbonate, potassium hydroxide and potassium hydrogencarbonate. The at least one potassium compound is in particular a potassium oxide ($K_2O$) or a mixed oxide. It is also possible to use another potassium compound which can be decomposed by heat. In the catalyst, the at least one potassium compound can typically be present as oxide mixed phase with the metals present in the catalyst.

The at least one potassium compound is typically comprised in an amount in the range from 1 to 30% by weight, preferably from 5 to 25% by weight, in particular preferably from 10 to 15% by weight, based on the total weight of the dehydrogenation catalyst and calculated as $K_2O$, in the dehydrogenation catalyst.

The potassium is preferably present in the form of one or more of the K/Fe mixed oxide phases described below, in the form of mixed oxides with other catalyst components, in particular with promoters, for example potassium molybdate, potassium tungstate, potassium vanadate, potassium manganate, and/or in the form of pure potassium phases, for example potassium oxide or potassium carbonate, in the finished catalyst.

According to the invention, the at least one iron compound and the at least one potassium compound are at least partly present in the form of one or more K/Fe mixed oxide phases of the general formula $K_xFe_yO_z$, where x is from 1 to 17; y is from 1 to 22 and z is from 2 to 34. These K/Fe mixed oxides or K/Fe mixed oxide phases are often referred to as potassium ferrites or potassium ferrite phases or as potassium ferrates or potassium ferrate phases.

For the purposes of the present invention, K/Fe mixed oxide phases are one or more potassium-iron mixed oxides of the formula $K_2O.nFe_2O_3$, where n is from 0.1 to 11. The potassium-iron mixed oxides can also be described by the formula $K_aFe_bO_c$, where a, b and c are natural numbers and a=1-17, b=1-22 and c=2-34. The K/Fe mixed oxide phases can be, in particular, at least one compound selected from the group consisting of $KFeO_2$, $K_2Fe_2O_4$ ($K_2O.Fe_2O_3$) (where n=1); $K_2Fe_8O_{13}$ ($K_2O.4Fe_2O_3$) (where n=4); $K_2Fe_{10}O_{16}$ ($K_2O.5Fe_2O_3$) (where n=5), $K_2Fe_{22}O_{34}$ ($K_2O.11Fe_2O_3$) (where n=11), $K_6Fe_2O_5$, $K_6Fe_2O_6$, $K_9(FeO_4)_2$ (space group C2/c) and $K_{17}Fe_5O_{16}$ (space group Cm). The K/Fe mixed oxide phase is preferably at least one compound selected from the group consisting of $K_2Fe_2O_4$($K_2O.Fe_2O_3$) (where n=1); $K_2Fe_8O_{13}$ ($K_2O.4Fe_2O_3$) (where n=4); $K_2Fe_{10}O_{16}$ ($K_2O.5Fe_2O_3$) (where n=5) and $K_2Fe_{22}O_{34}$ ($K_2O.11Fe_2O_3$) (where n=11).

The above-described K/Fe mixed oxide phases and mixtures thereof can be described by the general formula $K_xFe_yO_z$, where x is from 1 to 17, y is from 1 to 22 and z is from 2 to 34.

K/Fe mixed oxide phases can be formed by reaction of an iron compound, i.e. iron oxide, iron hydroxide, iron oxyhydroxide or other iron salts, and a potassium compound, e.g. potassium oxide, potassium hydroxide or other potassium salts, at elevated temperatures. The crystalline composition of the catalyst can be determined qualitatively and quantitatively by X-ray crystallography.

According to the invention, the dehydrogenation catalyst comprises at least 50% by weight, preferably at least 60% by weight, particularly preferably at least 65% by weight, based on the total catalyst, of the one or more K/Fe mixed oxide phases. The catalyst more particularly comprises from 50 to 89% by weight, preferably from 60 to 89% by weight, in particular from 65 to 85% by weight, based on the total catalyst, of the one or more K/Fe mixed oxide phases.

Preference is given to dehydrogenation catalysts in which the major part of the iron used in production is present in the form of one or more K/Fe mixed oxide phases of the general formula $K_xFe_yO_z$, as described above. It is possible for some of the iron to be present in the form of other iron oxides, for example in the form of iron oxide phases such as FeOOH, $Fe_2O_3$, in particular $\alpha$-$Fe_2O_3$ (hematite), and $Fe_3O_4$, (magnetite). A proportion of the iron used can preferably be present as hematite ($\alpha$-$Fe_2O_3$) in the finished dehydrogenation catalyst.

In particular, at least 50% by weight, preferably at least 70% by weight, in particular preferably at least 80% by weight, of the iron, based on the total amount of the iron used, calculated as $Fe_2O_3$, is present in the form of one or more of the above-described K/Fe mixed oxide phases of the general formula $K_xFe_yO_z$. In particular, from 0 to 50% by weight, preferably from 0 to 30% by weight, in particular preferably from 0 to 20% by weight, of the iron used, calculated as $Fe_2O_3$, can be present in the form of a hematite phase ($\alpha$(alpha)-$Fe_2O_3$).

According to the invention, the dehydrogenation catalyst comprises at least one cerium compound or at least one cerium compound is used in the production of the dehydrogenation catalyst. The at least one cerium compound is preferably selected from among cerium oxides, cerium hydroxides, cerium carbonates, water-containing cerium carbonates and cerium oxalates. Mixtures of the cerium compounds mentioned can preferably be used. The at least one cerium compound is preferably selected from among cerium(IV) oxide ($CeO_2$), cerium(III) oxide ($Ce_2O_3$), cerium(III) oxalate and cerium(III) carbonate, preferably from among cerium(IV) oxide ($CeO_2$) and cerium(II) carbonate. The at least one cerium compound is typically converted into cerium dioxide, in particular crystalline cerium dioxide during production of the catalyst.

According to the invention, the dehydrogenation catalyst comprises from 11 to 24% by weight, preferably from 12.5 to 22% by weight, particularly preferably from 15 to 20% by weight, of at least one cerium compound, calculated as $CeO_2$.

Cerium is typically comprised predominantly in the form of cerium dioxide, in particular as crystalline cerium dioxide, in particular as crystalline cerium dioxide in the form of cerianite, in the catalyst. The cerium can optionally also be at least partly present as mixed compounds, in particular as mixed oxide, with other catalyst components in the catalyst.

In particular, the catalyst comprises cerium dioxide crystallites which consist essentially of crystalline cerium dioxide, preferably crystalline dioxide in the form of cerianite, and are present as finely disperse crystallite grains having an average diameter of from 10 to 30 nm, preferably from 12 to 25 nm, particularly preferably from 14 to 22 nm, very particularly preferably from 16 to 19 nm.

In particular, at least 50% by weight, preferably at least 60% by weight, preferably at least 80% by weight, in particular at least 90% by weight, of the cerium, based on the total amount of cerium used, calculated as $CeO_2$, is present in the form of the above-described crystalline cerium dioxide having the crystallite size described.

In a preferred embodiment, the above-described catalyst of the invention comprises from 11 to 24% by weight, preferably from 12.5 to 22% by weight, particularly preferably from 15 to 20% by weight, of the at least one cerium compound, calculated as $CeO_2$, and from 50 to 90% by weight, preferably from 60 to 80% by weight, in particular from 65 to 75% by weight, based on the total catalyst, of the K/Fe mixed oxide phases.

The dehydrogenation catalyst preferably comprises at least one alkaline earth metal compound as further component, or at least one alkaline earth metal component is used in the production of the dehydrogenation catalyst. In particular, the dehydrogenation catalyst can comprise from 0.1 to 20% by weight, preferably from 0.1 to 10% by weight, in particular from 1 to 5% by weight, of at least one alkaline earth metal compound, calculated as oxide, as further component.

In a preferred embodiment, the dehydrogenation catalyst comprises at least one magnesium compound as further component. The dehydrogenation catalyst preferably comprises from 0.1 to 10% by weight, preferably from 1 to 5% by weight, of at least one magnesium compound, calculated as MgO, as further component. In particular, the at least one magnesium compound is selected from among magnesium oxide, magnesium carbonate and magnesium hydroxide.

The at least one magnesium compound is preferably magnesium oxide (MgO) and/or magnesium carbonate (MgCO$_3$). Preference is given to using magnesium oxide (MgO) and/or magnesium carbonate (MgCO$_3$) as further component in the production of the catalyst.

In a preferred embodiment, the dehydrogenation catalyst comprises at least one calcium compound as further component. The dehydrogenation catalyst preferably comprises from 0.1 to 10% by weight, preferably from 1 to 5% by weight, of at least one calcium compound, calculated as CaO, as further component. In particular, the at least one calcium compound is selected from among calcium oxide, calcium carbonate and calcium hydroxide. The at least one calcium compound is preferably calcium oxide (CaO). Preference is given to using calcium oxide (CaO) and/or calcium hydroxide (Ca(OH)$_2$) as further component in the production of the catalyst.

In a preferred embodiment, the dehydrogenation catalyst comprises at least one magnesium compound and at least one calcium compound. In particular, the dehydrogenation catalyst comprises from 0.1 to 10% by weight, preferably from 1 to 5% by weight, of at least one magnesium compound, calculated as MgO, and also from 0.1 to 10% by weight, preferably from 1 to 5% by weight, of at least one calcium compound, calculated as CaO.

A preferred embodiment of the present invention provides a dehydrogenation catalyst comprising
  from 50 to 80% by weight, preferably from 60 to 80% by weight, of at least one iron compound, calculated as Fe$_2$O$_3$;
  from 1 to 30% by weight, preferably from 5 to 25% by weight, particularly preferably from 10 to 20% by weight, of at least one potassium compound, calculated as K$_2$O;
  from 11 to 24% by weight, preferably from 12.5 to 22% by weight, particularly preferably from 15 to 20% by weight, of at least one cerium compound, calculated as CeO$_2$;
  from 0.1 to 10% by weight, preferably from 0.1 to 5% by weight, of at least one magnesium compound, calculated as MgO;
  from 0.1 to 10% by weight, preferably from 0.1 to 5% by weight, of at least one calcium compound, calculated as CaO;
  from 0 to 30% by weight, preferably from 0.0001 to 10% by weight, of at least one further component.

In a preferred embodiment, the abovementioned components add up to 100% by weight.

The further components can be comprised or be added in the production of the catalyst in amounts of from 0 to 30% by weight, preferably from 0 to 20% by weight, preferably from 0.0001 to 10% by weight, in particular from 0.001 to 5% by weight, in particular from 0.5 to 5% by weight.

The dehydrogenation catalyst can typically comprise one or more of the usual compounds for increasing the activity and/or selectivity as at least one further component, in particular as promoter or dopant. For example, at least one compound selected from compounds encompassing a metal selected from the group consisting of Mn, Ti, Cr, Co, Ni, Cu, Zn, Al, Ga, Ge, Zr, Nb, Ru, Rh, Pd, Ag, Cd, In, Sn, Sb, La, Hf, Ta, Re, Ir, Pt, Au, Pb and Bi can be comprised as further component, or at least one such compound is used in the production of the dehydrogenation catalyst. It is also possible for one or more of the abovementioned components to be comprised partly or entirely in a different raw material used in production of the catalyst, for example in the iron oxide. The customary components mentioned, in particular promoters or dopants, can typically be comprised in amounts of from 0 to 10% by weight, preferably from 0.0001 to 5% by weight, preferably from 0.001 to 2% by weight, in each case calculated as oxide in the highest oxidation state, based on the total catalyst.

The dehydrogenation catalyst can preferably comprise at least one compound selected from compounds encompassing a metal selected from the group consisting of molybdenum (Mo), titanium (Ti), vanadium (V) and tungsten (W) as further component; or at least one such compound is used in the production of the dehydrogenation catalyst. The further compound can in particular be selected from among oxygen compounds, for example oxides, oxide hydrates, oxo compounds, of molybdenum (Mo), titanium (Ti), vanadium (V) and tungsten (W). In particular, the at least one compound selected from compounds encompassing a metal selected from the group consisting of molybdenum (Mo), titanium (Ti), vanadium (V) and tungsten (W) is a compound which decomposes under the action of heat in the production of the dehydrogenation catalyst.

The dehydrogenation catalyst preferably comprises from 0.0001 to 10% by weight, preferably from 0.001 to 5% by weight, particularly preferably from 0.02 to 5% by weight, of at least one compound selected from the group consisting of molybdenum (Mo), titanium (Ti), vanadium (V) and tungsten (W), calculated as oxide in the highest oxidation state in each case, as further component.

The dehydrogenation catalyst preferably comprises from 0.0001 to 10% by weight, preferably from 0.001 to 5% by weight, particularly preferably from 0.02 to 5% by weight, of at least one compound selected from compounds encompassing a metal selected from the group consisting of molybdenum (Mo), titanium (Ti), vanadium (V) and tungsten (W), calculated as oxide in the highest oxidation state in each case, as further component.

Preference is given to using at least one molybdenum compound selected from among molybdenum oxides and molybdates (e.g. ammonium molybdate, potassium molybdate) as at least one further component. The at least one molybdenum compound is preferably molybdenum oxide.

In particular, the dehydrogenation catalyst preferably comprises from 0.1 to 10% by weight, preferably from 0.5 to 5% by weight, in particular from 1 to 4% by weight, of at least one molybdenum compound, calculated as MoO$_3$, as further component.

In particular, the dehydrogenation catalyst preferably comprises at least one titanium compound as further component; or at least one titanium compound can be used in the production of the dehydrogenation catalyst. The dehydrogenation catalyst can comprise from 0 to 1000 ppm, in particular from 1 to 1000 ppm, preferably from 10 to 500 ppm, preferably from 30 to 500 ppm, particularly preferably from 50 to 220 ppm, of the at least one titanium compound, calculated as TiO$_2$, based on the total catalyst.

The at least one titanium compound can in particular be selected from among titanium oxides, titanium alkoxides and titanium carboxylates. The at least one titanium compound is preferably titanium dioxide (TiO$_2$). The at least one titanium compound is preferably added as titanium dioxide (TiO$_2$) in the production of the catalyst. However, it is also possible to use other titanium compounds. It is additionally possible for the at least one titanium compound to be partly or entirely comprised in a different raw material used in catalyst production, e.g. in the iron oxide.

In particular, the dehydrogenation catalyst can comprise from 0.1 to 10% by weight, particularly preferably from 1 to 5% by weight, of at least one vanadium compound, calculated as $V_2O_5$, as further component.

In a preferred embodiment, the present invention provides a dehydrogenation catalyst as described above comprising:
from 50 to 80% by weight, preferably from 60 to 80% by weight, of at least one iron compound, calculated as $Fe_2O_3$;
from 1 to 30% by weight, preferably from 5 to 25% by weight, particularly preferably from 10 to 20% by weight, of at least one potassium compound, calculated as $K_2O$;
from 11 to 24% by weight, preferably from 12.5 to 22% by weight, particularly preferably from 15 to 20% by weight, of at least one cerium compound, calculated as $CeO_2$;
from 0.1 to 10% by weight, preferably from 1 to 5% by weight, of at least one magnesium compound, calculated as MgO;
from 0.1 to 10% by weight, preferably from 1 to 5% by weight, of at least one calcium compound, calculated as CaO;
from 0.0001 to 10% by weight, preferably from 0.001 to 5% by weight, of at least one compound selected from compounds encompassing a metal selected from the group consisting of molybdenum (Mo), titanium (Ti), vanadium (V) and tungsten (W), in each case calculated as the oxide in the highest oxidation state.

In a preferred embodiment, the abovementioned components add up to 100% by weight.

In a preferred embodiment, the present invention provides a dehydrogenation catalyst as described above comprising:
from 50 to 80% by weight, preferably from 60 to 80% by weight, of at least one iron compound, calculated as $Fe_2O_3$;
from 1 to 30% by weight, preferably from 5 to 25% by weight, particularly preferably from 10 to 20% by weight, of at least one potassium compound, calculated as $K_2O$;
from 11 to 24% by weight, preferably from 12.5 to 22% by weight, particularly preferably from 15 to 20% by weight, of at least one cerium compound, calculated as $CeO_2$;
from 0.1 to 10% by weight, preferably from 1 to 5% by weight, of at least one magnesium compound, calculated as MgO;
from 0.1 to 10% by weight, preferably from 1 to 5% by weight, of at least one calcium compound, calculated as CaO;
from 0.1 to 10% by weight, preferably from 0.1 to 5% by weight, in particular from 1 to 4% by weight, of at least one molybdenum compound, calculated as $MoO_3$;
from 1 to 1000 ppm, preferably from 10 to 500 ppm, preferably from 30 to 500 ppm, in particular from 50 to 220 ppm, of at least one titanium compound, calculated as $TiO_2$.

In a preferred embodiment, the abovementioned components add up to 100% by weight.

All figures in % by weight relate, unless indicated otherwise, to the total dehydrogenation catalyst. All figures in % by weight have, unless indicated otherwise, been calculated on the basis of the oxide of the respective metal in each case in the highest oxidation state.

In an embodiment, the above-described dehydrogenation catalyst comprises at least one further rare earth metal compound apart from cerium, in particular selected from the group consisting of lanthanum (La), praseodymium (Pr) and neodymium (Nd), as further component. The dehydrogenation catalyst preferably comprises from 1 to 1000 ppm, preferably from 10 to 500 ppm, particularly preferably from 20 to 300 ppm, of at least one further rare earth metal compound apart from cerium, calculated as oxide in the highest oxidation state in each case. In particular, the catalyst comprises from 1 to 1000 ppm, preferably from 10 to 500 ppm, particularly preferably from 20 to 300 ppm, of at least one rare earth metal compound selected from the group consisting of lanthanum, praseodymium and neodymium. The dehydrogenation catalyst can preferably comprise from 1 to 1000 ppm, preferably from 3 to 500 ppm, particularly preferably from 10 to 100 ppm, of at least one lanthanum compound, calculated as $La_2O_3$, as further component. The dehydrogenation catalyst can preferably comprise from 1 to 1000 ppm, preferably from 3 to 500 ppm, particularly preferably from 10 to 100 ppm, of at least one praseodymium compound, calculated as $PrO_2$, as further component. The dehydrogenation catalyst can preferably comprise from 1 to 1000 ppm, preferably from 3 to 500 ppm, particularly preferably from 10 to 100 ppm, of at least one neodymium compound, calculated as $Nd_2O_3$, as further component.

The above-described dehydrogenation catalyst can preferably comprise at least one compound of metals of transition groups 8 to 12 of the Periodic Table as further component. The above-described dehydrogenation catalyst preferably comprises at least one compound of metals selected from the group consisting of manganese (Mn), ruthenium (Ru), osmium (Os), cobalt (Co), nickel (Ni), palladium (Pd), platinum (Pt), copper (Cu), silver (Ag), gold (Au) and zinc (Zn); preferably selected from the group consisting of cobalt (Co), manganese (Mn), palladium (Pd), copper (Cu) and zinc (Zn); particularly preferably selected from the group consisting of manganese (Mn), copper (Cu), and zinc (Zn), as further component. The above-described dehydrogenation catalyst can comprise, in particular, from 1 to 1000 ppm, preferably from 50 to 500 ppm, particularly preferably from 50 to 200 ppm, of at least one compound of metals of transition groups 8 to 12 of the Periodic Table, in each case calculated as oxide in the highest oxidation state, as further component. In a preferred embodiment, the above-described dehydrogenation catalyst comprises from 1 to 1000 ppm, preferably from 50 to 500 ppm, particularly preferably from 50 to 200 ppm, of at least one compound of metals selected from the group consisting of manganese (Mn), copper (Cu) and zinc (Zn), in each case calculated as oxide in the highest oxidation state. The dehydrogenation catalyst can preferably comprise from 1 to 2000 ppm, preferably from 30 to 2000 ppm, particularly preferably from 100 to 2000 ppm, of at least one manganese compound, calculated as $MnO_2$, as further component. The dehydrogenation catalyst can preferably comprise from 1 to 1000 ppm, preferably from 10 to 200, particularly preferably from 30 to 100 ppm, of at least one copper compound, calculated as CuO, as further component. The dehydrogenation catalyst can preferably comprise from 1 to 1000 ppm, preferably from 1 to 500 ppm, particularly preferably from 10 to 100 ppm, of at least one zinc compound, calculated as ZnO, as further component.

In addition, the dehydrogenation catalyst can comprise at least one compound of elements of main group 4 of the Periodic Table of the Elements as further component. The above-described dehydrogenation catalyst preferably comprises at least one compound selected from the group consisting of silicon (Si), germanium (Ge), tin (Sn), and lead (Pb) compounds, preferably at least one silicon compound, as further component. In particular, the dehydrogenation catalyst comprises from 1 to 1000 ppm, preferably from 5 to 500 ppm, particularly preferably from 10 to 100 ppm, of at least one compound selected from the group consisting of silicon (Si), germanium (Ge), tin (Sn) and lead (Pb) compounds, calculated as oxide in each case in the highest oxidation state. In one embodiment, the dehydrogenation catalyst described comprises from 1 to 1000 ppm, preferably from 5 to 500 ppm, particularly preferably from 10 to 100 ppm, of at least one silicon compound, calculated as $SiO_2$.

The above-described dehydrogenation catalyst can typically comprise at least one nonmetal selected from among nonmetals of main groups 5 to 7 of the Periodic Table, in particular selected from the group consisting of nitrogen, phosphorus, sulfur and chlorine, as nonmetal apart from oxygen.

In a further embodiment, the dehydrogenation catalyst comprises:
- from 50 to 80% by weight, preferably from 60 to 80% by weight, of at least one iron compound, calculated as $Fe_2O_3$;
- from 1 to 30% by weight, preferably from 5 to 25% by weight, particularly preferably from 10 to 20% by weight, of at least one potassium compound, calculated as $K_2O$;
- from 11 to 24% by weight, preferably from 12.5 to 22% by weight, particularly preferably from 15 to 20% by weight, of at least one cerium compound, calculated as $CeO_2$;
- from 0.1 to 10% by weight, preferably from 1 to 5% by weight, of at least one magnesium compound, calculated as MgO;
- from 0.1 to 10% by weight, preferably from 1 to 5% by weight, of at least one calcium compound, calculated as CaO;
- from 0.1 to 10% by weight, preferably from 0.1 to 5% by weight, in particular from 1 to 4% by weight, of at least one molybdenum compound, calculated as $MoO_3$;
- from 1 to 1000 ppm, preferably from 10 to 500% by weight, preferably from 30 to 500 ppm, in particular from 50 to 220 ppm, of at least one titanium compound, calculated as $TiO_2$;
- from 0 to 10% by weight, particularly preferably from 1 to 5% by weight, of at least one vanadium compound, calculated as $V_2O_5$, and
- from 1 to 10 000 ppm, preferably from 10 to 5000 ppm, in particular from 10 to 3000 ppm, of at least one further component selected from among lanthanum compounds, praseodymium compounds, neodymium compounds, nickel compounds, copper compounds, zinc compounds and silicon compounds, calculated in each case as oxide in the highest oxidation state.

In a preferred embodiment, the abovementioned components add up to 100% by weight.

All figures in % by weight are based, unless indicated otherwise, on the total dehydrogenation catalyst. All figures in % by weight were, unless indicated otherwise, calculated on the basis of the oxide of the metal concerned in the highest oxidation state in each case.

In particular, the present invention provides a dehydrogenation catalyst as described above for the catalytic dehydrogenation of hydrocarbons at a molar steam/hydrocarbon ratio of from 1 to 20; preferably in the range from 1 to 10; in particular in the range from 1 to 9, particularly preferably from 5 to 8.5.

Furthermore, the present invention provides a process for producing a dehydrogenation catalyst as described above, which comprises the following steps:
i) production of a catalyst premix by mixing of at least one iron compound, at least one potassium compound, from 11 to 24% by weight, preferably from 12.5 to 22% by weight, particularly preferably from 15 to 20% by weight, based on the finished catalyst, of at least one cerium compound, calculated as $CeO_2$; optionally further metal compounds, optionally further components and optionally at least one binder with a solvent;
ii) production of shaped catalyst bodies from the catalyst premix obtained in step i);
iii) drying of the shaped catalyst bodies and calcination of the shaped catalyst bodies.

In the process for producing a dehydrogenation catalyst, preference is given to using the iron compounds, potassium compounds, cerium compounds and further components, in particular further metal compounds, described above in relation to the dehydrogenation catalyst, preferably in the amounts described. The above-described components can optionally be used in the production process; one or more of the components is preferably present entirely or in part in one of the raw materials used, for example in the used iron oxide and/or cerium carbonate.

The basic procedure in the production of dehydrogenation catalysts is known to those skilled in the art. The production of the above-described dehydrogenation catalysts can be carried out, for example, as described in WO 99/49966 or U.S. Pat. No. 6,551,958.

The choice of the catalyst components (starting materials, raw materials) and the choice of the production conditions, in particular the calcination conditions, can be made in such a way that catalysts according to the invention having the proportion according to the invention of K/Fe mixed oxide phases are obtained. The K/Fe mixed oxide phases described are typically formed by reaction of iron compounds and potassium compounds during the final calcination of the catalyst in the presence of all other components of the catalyst. It is also possible, in a two-stage process, firstly to produce a catalyst intermediate comprising the potassium ferrite phases from iron compounds and potassium compounds without further components and then to mix the catalyst intermediate with the cerium compound and the further components and calcine this mixture again.

A production process which has very few steps, in particular very few calcination steps is particularly advantageous.

To produce the catalyst premix, the components, typically in the form of solid powders, are generally mixed and then mixed with a solvent, in particular water, optionally with addition of a binder. Mixing is preferably carried out by intimate mixing, e.g. by kneading, in a stirred vessel, mix-muller, mixer, kneader or extruder, preferably in a mix-muller, kneader or mixer. In this context, a solvent is, in particular, a liquid solvent and/or dispersion medium in which the solid catalyst components are dispersed.

As solvent, use is made of, in particular, water or a mixture of water and polar solvents, e.g. alcohols, esters. As binder (also plasticizer), it is possible to use, for example, alginate, starch, carboxymethylcellulose, hydroxyethylcellulose and polyvinyl alcohol. The binders are typically used in the form of a solution in water.

Shaped catalyst bodies are then typically produced, e.g. by extrusion or pressing, from the resulting catalyst premix and are subsequently dried and calcined.

The production of shaped catalyst bodies from the catalyst premix is typically carried out by extrusion or pressing (tableting). Examples of shaped catalyst bodies are cylinders (pellets), rings, star bodies and honeycomb bodies. The production of shaped catalyst bodies from the catalyst premix obtained in step i) is preferably carried out by means of extrusion.

After shaping, the moist shaped bodies are typically dried at temperatures of from 80° C. to 500° C., preferably from 120 to 350° C. Drying can, for example, take place in a drying oven (e.g. on metal trays), in a drying drum and/or on belt dryers.

The shaped bodies are then typically calcined. Calcination can be carried out in muffle furnaces, belt calciners, rotary tube furnaces, etc. The catalyst extrudates are preferably calcined in a rotary tube furnace.

The calcination of the shaped catalyst bodies in step iii) is preferably carried out at a temperature in the range from 500° C. to 1200° C., preferably from 600° C. to 900° C., in particular from 750° C. to 850° C.

The calcination of the shaped catalyst bodies in step iii) is preferably carried out a temperature in the range from 500° C. to 1200° C., preferably from 600° C. to 900° C., in particular from 750° C. to 850° C., and for a time of from 10 minutes to 300 minutes, preferably from 30 minutes to 300 minutes, particularly preferably from 30 minutes to 180 minutes.

The calcination in step iii) can preferably be carried out in a stationary process, for example in a muffle furnace, or in a continuous process, for example in a continuous rotary tube furnace.

As compounds and further components, it is possible to use compounds in the form in which they are present in the finished catalyst or compounds which are converted during the production process into compounds in the form in which they are present in the finished catalyst. Preference is given to using the compounds described in connection with the dehydrogenation catalyst of the invention.

In particular, the invention provides a process for producing a dehydrogenation catalyst as described, wherein an iron compound comprising at least 50% by weight, preferably at least 80% by weight, based on the total iron compound, of iron(III) oxide ($Fe_2O_3$) is used. Hematite ($Fe_2O_3$) is predominantly used as iron component. Part of the iron can be used as goethite (FeOOH) or magnetite ($Fe_3O_4$), with this proportion being able to be from 0 to 30%. In particular, the invention provides a process for producing a dehydrogenation catalyst as described, wherein a potassium oxide, potassium hydroxide, potassium carbonate and/or potassium hydrogencarbonate is used as potassium compound. As cerium compound, preference is given to using cerium oxides, in particular cerium dioxide, cerium carbonates, cerium hydroxides and/or cerium hydrogencarbonates. As magnesium compound, preference is given to using magnesium oxide, magnesium carbonate and/or magnesium hydroxide. As calcium compound, preference is given to using calcium oxide, calcium carbonate and/or calcium hydroxide. As titanium compound, preference is given to using titanium oxides, in particular $TiO_2$, titanium alkoxides and/or titanium carboxylates. As molybdenum compound, preference is given to using molybdenum oxides, in particular $MoO_3$. As vanadium compound, preference is given to using vanadium oxides.

In a further aspect, the present invention provides a process for the catalytic dehydrogenation of a hydrocarbon, wherein a mixture of steam and at least one hydrocarbon is brought into contact with a dehydrogenation catalyst as described above.

The preferred embodiments described above in connection with the dehydrogenation catalyst of the invention and the process for producing it apply analogously to the process of the invention for the catalytic dehydrogenation of a hydrocarbon.

The process for the catalytic dehydrogenation of a hydrocarbon using the dehydrogenation catalyst of the invention gives an improved yield, for example an improved styrene yield, compared to known processes or dehydrogenation catalysts.

The present invention preferably provides a process for the catalytic dehydrogenation of a hydrocarbon, wherein a mixture of steam and at least one hydrocarbon having a molar steam/hydrocarbon ratio in the range from 1 to 20; preferably from 1 to 10; in particular from 1 to 9; particularly preferably from 5 to 8.5 is used. In particular, the invention provides a process for the catalytic dehydrogenation of ethylbenzene to styrene, wherein a mixture of steam and ethylbenzene having a steam/hydrocarbon weight ratio in the range from 0.17 to 3.4; preferably from 0.17 to 1.7; in particular from 0.17 to 1.5; particularly preferably from 0.9 to 1.45 is used. The catalytic dehydrogenation according to the invention of a hydrocarbon can particularly preferably be carried out using an average steam/hydrocarbon weight ratio in the range from 0.9 to 1.45 (kg/kg).

In the process of the invention for catalytic dehydrogenation, yields of from 40 to 80%, preferably from 50 to 75%, particularly preferably from 60 to 70%, based on the hydrocarbon used, are typically achieved per pass through the reactor. In particular, styrene yields of 40 to 80%, preferably from 50 to 75%, particularly preferably from 60 to 70%, based on the ethylbenzene used, are achieved per pass through the reactor in the catalytic dehydrogenation of ethylbenzene. The yields indicated are based on mol %.

The process for the catalytic dehydrogenation of a hydrocarbon is typically carried out at temperatures of from 500 to 650° C. and pressures of from 0.2 to 2 bar absolute.

The process described can be the dehydrogenation of alkylaromatic or aliphatic hydrocarbons; it is preferably the dehydrogenation of alkylaromatic hydrocarbons, particularly preferably the dehydrogenation of ethylbenzene to styrene. The process of the invention for the dehydrogenation of a hydrocarbon can be, for example, the dehydrogenation of ethylbenzene to styrene, of isopropylbenzene to alpha-methylstyrene, of butene to butadiene or of isoamylene to isoprene. The hydrocarbon is preferably ethylbenzene.

Furthermore, the present invention provides for the use of a dehydrogenation catalyst as described above for the catalytic dehydrogenation of a hydrocarbon, in particular an alkylaromatic or aliphatic hydrocarbon, preferably an alkylaromatic hydrocarbon, particularly preferably ethylbenzene. The invention preferably provides for the use of a dehydrogenation catalyst as described above for the catalytic dehydrogenation of a hydrocarbon at a molar steam/hydrocarbon ratio in the range from 1 to 20; preferably in the range from 1 to 10; in particular in the range from 1 to 9; particularly preferably in the range from 5 to 8.5.

The FIGURE is explained below:

FIG. 1 shows the styrene yield Y in mol % in the catalytic dehydrogenation of ethylbenzene (as per examples 1 to 8) at a steam/ethylbenzene weight ratio of 1.25 kg/kg and a temperature of 620° C. as a function of the content of CeO$_2$ [%] in % by weight in the catalyst used (based on the total catalyst).

The styrene yield in mol % is in each case reported as molar amount of styrene produced based on the molar amount of ethylbenzene used.

The present invention is illustrated by the following examples.

EXAMPLES

Catalysts having essentially the same composition in respect of potassium oxide and promoters but comprise different amounts of cerium dioxide were produced. The variation in the cerium dioxide content was compensated by appropriate adaptation of the iron oxide content. The catalysts were used under the same conditions.

The catalysts were characterized by means of X-ray diffraction, with the content of K/Fe mixed oxide phases and the CeO$_2$ crystallite size being determined (see example 9).

Examples 1 to 3 (Comparative Examples)—Production of the Catalysts K1 to K3

Components used were iron oxide (alpha-Fe$_2$O$_3$, hematite), potassium carbonate (K$_2$CO$_3$), cerium carbonate (Ce$_2$CO$_3$), magnesium oxide (MgO), molybdenum oxide (MoO$_3$), calcium hydroxide (Ca(OH)$_2$) and titanium dioxide (TiO$_2$).

The abovementioned pulverulant components were firstly mixed dry and then kneaded with addition of water and starch solution. The catalyst composition was extruded, giving pellets having a diameter of 3 mm. The shaped catalyst bodies (pellets) were dried at 120° C. for 1 hour and at 350° C. for 1 hour and subsequently calcined at 805° C. for 1 hour in air in a muffle furnace.

A catalyst K1 having the following nominal oxide composition was obtained:

| | |
|---|---|
| 12.0% by weight of | K$_2$O, |
| 5.0% by weight of | CeO$_2$, |
| 2.1% by weight of | MgO, |
| 2.0% by weight of | CaO, |
| 2.4% by weight of | MoO$_3$, |
| 200 ppm of | TiO$_2$ |
| Balance | Fe$_2$O$_3$ (76.48% by weight) |

All figures are in % by weight, based on the total amount of catalyst. All figures relate, unless indicated otherwise, to the oxide of the metal concerned in the highest oxidation state.

Further catalysts (catalysts K2 and K3) were produced as described in comparative example 1; with the CeO$_2$ content being varied (7.5% by weight and 10% by weight). The change in the CeO$_2$ content was compensated by altering the Fe$_2$O$_3$ content.

The compositions of the catalysts are shown in table 1.

Examples 4 to 8—Production of the Catalysts K4 to K8

Further catalysts (catalysts K4 to K8) were produced as described in comparative example 1, with the CeO$_2$ content being varied (12.5% by weight, 15.0% by weight, 17.5% by weight, 20.0% by weight, 25.0% by weight). The change in the CeO$_2$ content was compensated by altering the Fe$_2$O$_3$ content.

The compositions of the catalysts are shown in table 1.

Example 9: Characterization of the Catalysts K1 to K8

The crystallographic phase compositions, e.g. content of K/Fe mixed oxide phases and cerium dioxide crystallite size, were determined by means of X-ray diffraction measurements using the following method:

The shaped catalyst bodies were milled to a fine powder in a mill. The samples were then introduced into a standard sample holder (from Bruker AXS GmbH) and struck smooth using a glass plate. The samples were measured in a D8 Advance Diffractometer (from Bruker AXS GmbH) using a variable orifice plate (V20—irradiated sample length of 20 mm) and an energy-dispersive point detector (Sol-X, from Bruker AXS GmbH) in the angle range from 10° to 55° 2θ (2 theta) using a step width of 0.02° 2θ (2 theta). The data were evaluated using the software TOPAS 4.2 (from Bruker AXS GmbH). The phase composition of the catalysts typically comprised variable proportions of various crystallographic phases, e.g. cerianite (CeO$_2$), hematite (Fe$_2$O$_3$), magnetite (Fe$_3$O$_4$), K$_2$CO$_3$.1.5H$_2$O, K$_4$H$_2$(CO$_3$)$_3$.1.5H$_2$O, KFe$_{11}$O$_{17}$, K$_2$Fe$_{10}$O$_{16}$, K$_6$Fe$_2$O$_5$, K$_6$Fe$_2$O$_6$, Kg(FeO$_4$)$_2$ (space group C2/c) and K$_{17}$Fe$_5$O$_{16}$ (space group Cm), K$_2$Fe$_2$O$_4$, KFeO$_2$ and possibly other oxidic phases which are dependent on the further metal compounds present. In all phases, the lattice parameters, crystallite size and scale were refined and in the case of KFe$_{11}$O$_{17}$ additionally the Gaussian component of the lattice strain and a March-Dollase preferential orientation in the (001) direction. The background was fitted using a third order polynominal, and the sample height error was refined. Intensity corrections for the Lorentz polarization were taken into account. The crystallite size is the value calculated by the TOPAS "Lvol FWHM" software.

The nominal compositions of the catalysts, the proportions of K/Fe mixed oxide phase and the CeO$_2$ crystallite sizes are summarized in table 1 below.

TABLE 1

| | composition of all catalysts (% by weight as oxide) | | | | | | | | |
|---|---|---|---|---|---|---|---|---|---|
| Catalyst | CeO$_2$ | K$_2$O | MgO | CaO | MoO$_3$ | TiO$_2$ ppm | Fe$_2$O$_3$ | Average CeO$_2$ crystallite size nm | K/Fe Mixed oxide phases % by weight |
| | | | % by weight | | | | | | |
| K1 | 5.0 | 12.0 | 2.1 | 2.0 | 2.4 | 200 | Balance | 25 | 90 |
| K2 | 7.5 | 12.0 | 2.1 | 2.0 | 2.4 | 200 | Balance | 25 | 76 |
| K3 | 10.0 | 12.0 | 2.1 | 2.0 | 2.4 | 200 | Balance | 24 | 74 |
| K4 | 12.5 | 12.0 | 2.1 | 2.0 | 2.4 | 200 | Balance | 23 | 71 |

TABLE 1-continued composition of all catalysts (% by weight as oxide)

| Catalyst | CeO$_2$ | K$_2$O | MgO | CaO | MoO$_3$ | TiO$_2$ ppm | Fe$_2$O$_3$ | Average CeO$_2$ crystallite size nm | K/Fe Mixed oxide phases % by weight |
|---|---|---|---|---|---|---|---|---|---|
| K5 | 15.0 | 12.0 | 2.1 | 2.0 | 2.4 | 200 | Balance | 23 | 71 |
| K6 | 17.5 | 12.0 | 2.1 | 2.0 | 2.4 | 200 | Balance | 24 | 68 |
| K7 | 20.0 | 12.0 | 2.1 | 2.0 | 2.4 | 200 | Balance | 23 | 65 |
| K8 | 25.0 | 12.0 | 2.1 | 2.0 | 2.4 | 200 | Balance | 24 | 60 |

Example 10 — Dehydrogenation of Ethylbenzene to Styrene at a Steam/Ethylbenzene Ratio of 1.25 kg/kg The catalysts K1 to K3 and K4 to K8 from examples 1 to 8 were used in the dehydrogenation of ethylbenzene to styrene in the presence of steam. The catalyst material obtained was comminuted and sieved, with a fraction of from 0.5 to 0.7 mm being separated off and used for the further experiments.

For each catalyst, two isothermal tube reactors were each filled with 13.3 ml of catalyst of the fraction having a particle size of from 0.5 to 0.7 mm. The reactors were in each case continuously supplied at 620° C. and 1 atm initial pressure with 14.6 g/h of ethylbenzene and 18.3 g/h of deionized (DI) water, corresponding to a water/ethylbenzene (S/HC) ratio of 1.25 kg/kg or 7.36 mol/mol. After stabilization, for instance after 40 hours, samples were taken from the liquid condensate and analyzed by gas chromatography. Conversion, selectivity and styrene yield were determined for each reactor. An average over the two reactors operated in parallel was determined for each catalyst. The results are shown in table 2.

TABLE 2 catalytic properties of the catalysts K1 to K8

| Catalyst | CeO$_2$ content % by weight | Average CeO$_2$ crystallite size nm | K/Fe Mixed oxide phases % by weight | Ethylbenzene conversion Mol % | Styrene selectivity Mol % | Styrene yield Mol % |
|---|---|---|---|---|---|---|
| K1 | 5.0 | 25 | 90 | 71.58 | 95.63 | 68.45 |
| K2 | 7.5 | 25 | 76 | 72.22 | 95.61 | 69.05 |
| K3 | 10.0 | 24 | 74 | 72.56 | 95.66 | 69.41 |
| K4 | 12.5 | 23 | 71 | 72.88 | 95.57 | 69.65 |
| K5 | 15.0 | 23 | 71 | 73.36 | 95.51 | 70.06 |
| K6 | 17.5 | 24 | 68 | 74.06 | 95.28 | 70.56 |
| K7 | 20.0 | 23 | 65 | 74.20 | 95.19 | 70.63 |
| K8 | 25.0 | 24 | 60 | 72.93 | 94.84 | 69.16 |

Ethylbenzene conversion, styrene selectivity and yield were determined by means of the following formulae:

Conversion (mol%)=[$A*M_f - B*M_p$)/($A*M_f$)]×100

Selectivity (mol%)=[$D*M_p - C*M_f$)/($A*M_f - B*M_p$)]× ($M_{EB}/M_{ST}$)×100

Yield (mol%)=Conversion×selectivity/100 where:
A: ethylbenzene concentration at the reactor inlet (% by weight)
B: ethylbenzene concentration at the reactor outlet (% by weight)
C: styrene concentration at the reactor inlet (% by weight)
D: styrene concentration at the reactor outlet (% by weight)
$M_f$: average molar mass of the organic starting materials
$M_p$: average molar mass of the organic products
$M_{EB}$: molar mass of ethylbenzene
$M_{ST}$: molar mass of styrene The abovementioned figures in respect of concentration and molar masses are in each case based on the organic phase (without water).

The data in table 2 show that the catalysts K4 to K7 having a cerium dioxide content in the range from 12.5 to 20% by weight give significantly higher styrene yields than the catalysts from comparative examples K1 to K3 which have lower proportions of cerium dioxide. The data in table 2 also show that an excessively high cerium dioxide content reduces the content of K/Fe mixed oxide phases and the catalyst gives a lower styrene yield (catalyst 8). The highest yields are obtained using the catalysts from examples 5, 6 and 7 which have a cerium dioxide content in the range from 15 to 20% by weight and a proportion of K/Fe mixed oxide phases of at least 65% by weight.

Furthermore, it can be seen from table 2 that the particle size of the cerium dioxide particles in the series of experiments stays approximately the same.

FIG. 1 shows the styrene yield Y [%] as a function of the proportion of CeO$_2$ in % by weight [% CeO$_2$] in the catalyst. It can very clearly be seen that an optimal styrene yield can be obtained in the range from 11 to 24% by weight of CeO$_2$.

An optimal content of cerium dioxide in the range from 11 to 24% by weight, preferably from 12.5 to 22% by weight, in particular from 15 to 20% by weight, was found.

The invention claimed is:
1. A dehydrogenation catalyst comprising
at least one iron compound,
at least one potassium compound and
from 15 to 20% by weight, based on the total catalyst, of at least one cerium compound, calculated as CeO$_2$,
wherein the at least one iron compound and the at least one potassium compound are at least partly present in the form of one or more K/Fe mixed oxide phases of the general formula

$K_xFe_yO_z$, where x is from 1 to 17; y is from 1 to 22 and z is from 2 to 34, where the catalyst comprises from 65 to 85% by weight, based on the total catalyst, of the one or more K/Fe mixed oxide phases.

2. The dehydrogenation catalyst according to claim 1, wherein the catalyst comprises from 0.1 to 20% by weight, of at least one alkaline earth metal compound, calculated as oxide, as further component.

3. The dehydrogenation catalyst according to claim 1, wherein the catalyst comprises from 0.0001 to 10% by weight, of at least one compound selected from compounds encompassing a metal selected from the group consisting of molybdenum, titanium, vanadium and tungsten, calculated as oxide in the highest oxidation state in each case, as further component.

4. The dehydrogenation catalyst according to claim 1, wherein the catalyst comprises
from 50 to 80% by weight of at least one iron compound, calculated as $Fe_2O_3$;
from 1 to 30% by weight of at least one potassium compound, calculated as $K_2O$;
from 15 to 20% by weight of at least one cerium compound, calculated as $CeO_2$;
from 0.1 to 10% by weight of at least one magnesium compound, calculated as MgO;
from 0.1 to 10% by weight of at least one calcium compound, calculated as CaO;
from 0.0001 to 10% by weight, of at least one compound selected from compounds encompassing a metal selected from the group consisting of molybdenum (Mo), titanium (Ti), vanadium (V) and tungsten (W), in each case calculated as the oxide in the highest oxidation state.

5. The dehydrogenation catalyst according to claim 1, wherein the catalyst comprises
from 50 to 80% by weight of at least one iron compound, calculated as $Fe_2O_3$;
from 1 to 30% by weight of at least one potassium compound, calculated as $K_2O$;
from 15 to 20% by weight of at least one cerium compound, calculated as $CeO_2$;
from 0.1 to 10% by weight of at least one magnesium compound, calculated as MgO;
from 0.1 to 10% by weight of at least one calcium compound, calculated as CaO;
from 0.1 to 10% by weight of at least one molybdenum compound, calculated as $MoO_3$;
from 1 to 1000 ppm of at least one titanium compound, calculated as $TiO_2$.

6. The dehydrogenation catalyst according to claim 1, wherein the catalyst comprises
from 50 to 80% by weight of at least one iron compound, calculated as $Fe_2O_3$;
from 1 to 30% by weight of at least one potassium compound, calculated as $K_2O$;
from 15 to 20% by weight of at least one cerium compound, calculated as $CeO_2$;
from 0.1 to 10% by weight of at least one magnesium compound, calculated as MgO;
from 0.1 to 10% by weight of at least one calcium compound, calculated as CaO;
from 0.1 to 10% by weight of at least one molybdenum compound, calculated as $MoO_3$;
from 1 to 1000 ppm of at least one titanium compound, calculated as $TiO_2$.

7. A process for producing a dehydrogenation catalyst according to claim 1, which comprises the following steps
   i) producing a catalyst premix by mixing of at least one iron compound, at least one potassium compound, from 15 to 20% by weight, based on the finished catalyst, of at least one cerium compound, calculated as $CeO_2$; optionally further metal compounds, optionally further components and optionally at least one binder with a solvent;
   ii) producing shaped catalyst bodies from the catalyst premix obtained in step i);
   iii) drying of the shaped catalyst bodies and calcination of the shaped catalyst bodies.

8. The process for producing a dehydrogenation catalyst according to claim 7, wherein the calcination of the shaped catalyst bodies in step iii) is carried out at a temperature in the range from 500 to 1200° C.

9. A process for the catalytic dehydrogenation of a hydrocarbon, wherein a mixture of steam and at least one hydrocarbon is brought into contact with a dehydrogenation catalyst according to claim 1.

10. The process for the catalytic dehydrogenation of a hydrocarbon according to claim 9, wherein a mixture of steam and at least one hydrocarbon having a molar steam/hydrocarbon ratio in the range from 1 to 10 is used.

11. The process for the catalytic dehydrogenation of a hydrocarbon according to claim 9, wherein the hydrocarbon is ethylbenzene.

\* \* \* \* \*